United States Patent [19]

Ratton et al.

[11] Patent Number: 4,551,558
[45] Date of Patent: Nov. 5, 1985

[54] BROMINATION OF SUBSTITUTED BENZALDEHYDES

[75] Inventors: Serge Ratton, La Verpilliere; Jean-Luc Bougeois, Sainte-Foy les Lyon, both of France

[73] Assignee: Rhone-Poulenc Specialites Chimiques, Courbevoie, France

[21] Appl. No.: 685,373

[22] Filed: Dec. 24, 1984

[30] Foreign Application Priority Data

Dec. 22, 1983 [FR] France .................................. 83 20798

[51] Int. Cl.$^4$ ............................................. C07C 45/63
[52] U.S. Cl. ...................................... 568/433; 568/442
[58] Field of Search ................................. 568/433, 437

[56] References Cited

U.S. PATENT DOCUMENTS 4,335,263  6/1982  Minai .................................... 568/437

Primary Examiner—Bernard Helfin
Attorney, Agent, or Firm—Burns, Doane, Swecker & Mathis

[57] ABSTRACT

Substituted bromobenzaldehydes, e.g., 5-bromovanillin, are facilely prepared with overall avoidance of HBr by-product, by (i) first brominating the corresponding benzaldehyde with a less than stoichiometric amount of bromine, and (ii) completing said bromination reaction with a brominating couple which comprises (1) the hydrobromic acid generated in situ in the step (i) and (2) a bromide ion oxidizer.

17 Claims, No Drawings

BROMINATION OF SUBSTITUTED BENZALDEHYDES

CROSS-REFERENCE TO RELATED APPLICATION

Our copending application Ser. No. 685,372, filed concurrently herewith, and assigned to the assignee hereof.

BACKGROUND OF THE INVENTION

1. Field of the Invention

The present invention relates to the preparation of bromobenzaldehydes bearing hydroxy and/or alkoxy substituents, and in particular the compound 5-bromovanillin.

2. Description of the Prior Art

Bromobenzaldehydes bearing hydroxy and/or alkoxy substituents are known to this art as valuable industrial compounds useful as intermediates in various organic syntheses. Thus, 5-bromovanillin (3-bromo-4-hydroxy-5-methoxybenzaldehyde), bromoprotocatechuic aldehyde (3-bromo-4,5-dihydroxybenzaldehyde) and 3-bromo-4,5-dimethoxybenzaldehyde are useful as intermediates in the preparation of 3,4,5-trimethoxybenzaldehyde which is itself an intermediate for the preparation of such pharmaceuticals as trimethoprim 2,4-diamino-5-(3,4,5-trimethoxybenzyl)pyrimidine. These bromobenzaldehydes are also useful in the preparation of bromophenylalanines having hypotensive activity (cf. French Pat. No. 1,592,518).

The alkoxy and/or hydroxy substituted bromobenzaldehydes are typically prepared by reacting bromine with the corresponding aldehyde.

And a variety of methods are known for brominating aromatic aldehydes. Thus, it has been proposed to carry out the bromination of hydroxy and/or alkoxybenzaldehydes in various reaction media. The solvent employed most generally is glacial acetic acid containing, if appropriate, an alkali metal acetate, such as sodium acetate (cf. Dakin, *Am. Chem. Journal*, 42, 477–98 (1909); Torrey et al, *J. Am. Chem. Soc.*, 31, 583–585 (1909); O. S. Brady et al, *J. Chem. Soc.*, 107, 1858–62 (1915); E. I. Shriner et al, *J. Am. Chem. Soc.*, 51, 2194 (1929); R. A. McIvor et al, *Can. J. of Chem.*, 32, 298–302 (1953); Henry et al, *J. Chem. Soc.*, 2279–89 (1930); F. Misani et al, *J. Org. Chem.*, 10, 356 (1945); R. Pschorr, *Ann.*, 391, 23–39 (1912); French Pat. No. 1,592,518). Although this process results in excellent yields of bromobenzaldehydes, particularly in the case of vanillin, it suffers from various disadvantages which make it unattractive from an industrial standpoint. In particular, upon completion of the reaction this process gives rise to a solution of hydrobromic acid in acetic acid from which it is difficult, if not impossible in practice, to recover HBr.

It has also been proposed (cf. R. Pschorr, loc. cit.) to replace the glacial acetic acid with chloroform; in this instance it is difficult to separate the bromobenzaldehyde from the hydrobromic acid contained therein by washing with chloroform, which suggests using a third solvent for the washing and thus making the process too complicated to exploit industrially.

In French Pat. No. 72/38,410, published under No. 2,177,693, a process for brominating vanillin has been described, consisting of adding a solution of vanillin in hydrobromic acid, containing 48% by weight of HBr, to bromine.

Lower alcohols, and particularly ethanol, have also been employed as bromination reaction media (cf. F. Tiemann et al, Ber, 7, 615 [1874]). The conjoint formation of irrecoverable methyl bromide or ethyl bromide which may be difficult to justify economically in large-scale production of bromovanillin makes this process unattractive.

In every instance the reaction leads to the formation of one molecule of hydrobromic acid per molecule of bromobenzaldehydes produced in accordance with the following reaction scheme:

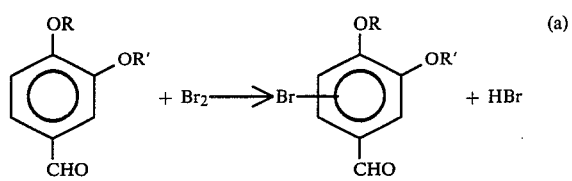

It is found that in such a process only one half of the bromine employed is consumed to form bromobenzaldehydes, with the other half forming hydrobromic acid or, depending upon the solvent employed, alkyl bromides. Recovery and/or economical disposition of these by-products reduce the industrial interest of this process, whatever its application.

From this analysis of the state of the art it follows, therefore, that the conjoint formation of HBr resulting from the use of bromine as a brominating agent presents a serious problem in the industrial application of the known processes.

SUMMARY OF THE INVENTION

Accordingly, a major object of the present invention is the provision of an improved process for the bromination of substituted benzaldehydes, which improved process completely avoids those disadvantages and drawbacks above outlined with respect to the conjoint production of hydrobromic acid.

Briefly, the present invention features the preparation of substituted bromobenzaldehydes having the formula:

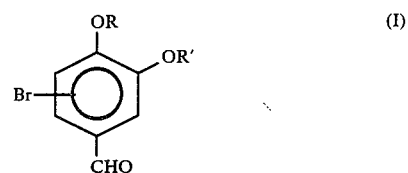

in which R and R', which are identical or different, denote a hydrogen atom or a methyl or ethyl radical, and comprising reacting a substituted aldehyde of the general formula:

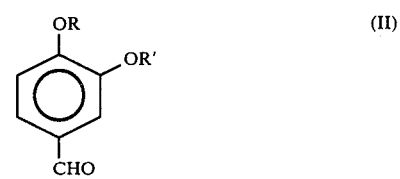

with bromine, which bromination is initially carried out utilizing an amount of bromine which is less than the stoichiometric amount required for complete reaction and in which the bromination reaction is completed by using the pair or couple which comprises the hydrobromic acid generated during the initial reaction and an oxidizer for bromide ions.

DETAILED DESCRIPTION OF THE INVENTION

More particularly according to the present invention, the bromide ion oxidizer is advantageously any compound suited for such purpose, especially hydrogen peroxide, nitric acid, and hypochlorite ions, particularly in the form of the alkali metal hypochlorites.

Although it is generally known to this art to oxidize bromide ions to bromine with the aid of certain oxidants, the use of the HBr/oxidizer pair to effect bromination of hydroxy and/or alkoxy benzaldehydes would have been a cause for concern about the course of the oxidation and/or substitution reactions of the starting products. Thus, the prior art teaches oxidation of the aldehyde group with hydrogen peroxide according to a reaction of the Baeyer and Williger type (cf. C. H. Hassal, *Organic Reactions*, 9, pages 73 to 106 [1957]; J. E. Leffler, *Chem. Rev.*, 45, pages 385 to 410 [1949]. Accordingly, it would not have been expected that the hydroxy and/or alkoxy substituted aromatic aldehydes could be brominated consistent with the reaction mechanism hereof, without concomitant oxidation of the aldehyde functions.

Without wishing to be bound to any particular theory or explanation, it is considered that the overall mechanism of the invention proceeds according to the following reactions:

(a) partial bromination of the aldehyde utilizing a stoichiometric deficit of bromine according to the reaction scheme:

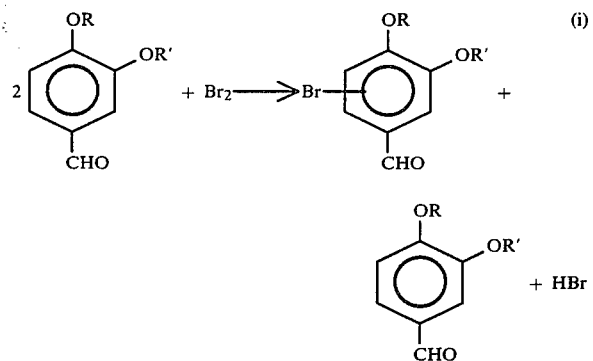

(b) complete bromination of the unconverted aldehyde using the HBr/oxidizer pair; thus, in the instance where the latter comprises hydrogen peroxide, the reaction may be represented by the scheme:

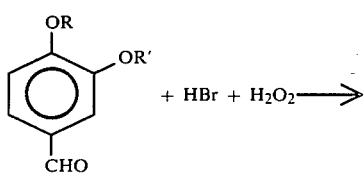

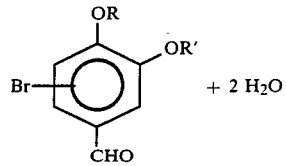

The overall balanced reaction may then be represented by the scheme:

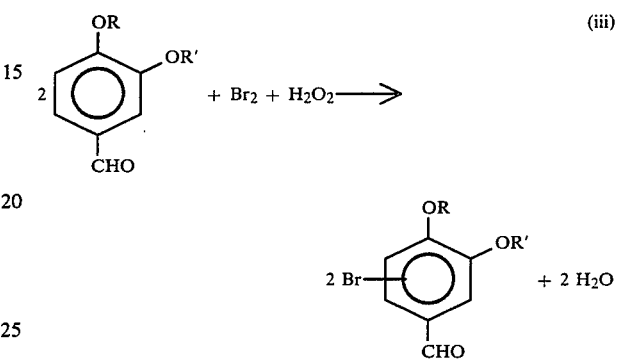

The process according to the invention thus makes it possible to completely brominate substituted benzaldehydes with bromine and to directly utilize the bromine comprising the hydrobromic acid initial reaction by-product.

Although the bromination according to the invention may be carried out in water and/or an inert, preferably water-immiscible organic solvent, such as halogenated aliphatic hydrocarbons or ethers, it is preferable, to obtain the highest yields and degrees of conversion to carry out the reaction in the presence of an aliphatic or inorganic acid which is inert to bromine or the oxidizer. In this instance the amount of acid expressed as molar equivalent per mole of benzaldehyde is preferably at least equal to 0.001 equivalent per mole of benzaldehyde and more preferably at least 0.01 equivalent per mole of benzaldehyde. There is no critical upper limit on the amount of acid, the latter being capable of forming the reaction medium.

In one particular embodiment, the process according to the invention is carried out in an alkanoic acid containing from 2 to 7 carbon atoms, such as acetic, propionic, butyric, n-pentanoic or n-hexanoic acids. Preferably, acetic acid is used, in which the starting material benzaldehydes are soluble and which may constitute the reaction medium. Equally well, an aqueous solution of acid may be used, the concentration of which is not critical, or an anhydrous acid.

In a second embodiment the process is carried out in the presence of an inorganic acid which may also at least partially constitute the reaction medium. Preferably, aqueous solutions of hydrobromic and sulfuric acids are used, the concentrations of which are not critical and may vary over wide limits. Thus, it is possible to use aqueous solutions of sulfuric acid containing from 5 to 65% by weight of $H_2SO_4$ or aqueous solutions of hydrobromic acid containing from 5 to 60% by weight of HBr. In the latter instance solutions are preferably used containing from 45 to 55% by weight of HBr because the solubility of the starting material aldehydes increases with the HBr concentration. In a preferred embodiment of the invention the aqueous solution of inorganic acid at least partially constitutes the reaction medium. Thus, the bromination may be carried out on a suspension of benzaldehyde in an aqueous solution of $H_2SO_4$ or of HBr or on a solution of benzaldehydes in a concentrated solution of HBr. It is also possible to employ together with the acidic aqueous solution an organic solvent for benzaldehyde and for bromine, which is inert under the reaction conditions, and preferably water-immiscible; an organic phase containing the benzaldehyde is then contacted with an acidic aqueous phase in which the bromide ions are oxidized. This is a preferred embodiment of the process according to the invention. The embodiment comprising the use of an aqueous solution of hydrobromic acid and an organic solvent is particularly highly suitable according to the invention. Among the solvents which are suitable for implementing this embodiment, representative are the halogenated hydrocarbons (e.g., methylene chloride, chloroform, carbon tetrachloride), and the aliphatic ethers (e.g., isopropyl ether, amyl ether, butyl ethyl ether, t-butyl ethyl ether, n-butyl ether, n-propyl ether, and n-butyl methyl ether).

The concentration of the starting aromatic aldehyde in the reaction medium selected is also not critical and may vary over wide limits. This depends mainly on practical factors such as the stirrability of the reaction mixture and the productivity of the process.

Although the amount of bromine employed in the process according to the invention, expressed in moles per mole of aldehyde, may vary somewhat provided that it remains below the stoichiometric amount resulting from the scheme (a), it is preferable that this amount remains close to one half of such stoichiometric amount when the intention is to avoid or reduce as much as possible the loss of bromine in the form of hydrobromic acid. Thus, the amount of bromine preferably ranges from 0.45 to 0.65 mole of bromine per mole of benzaldehyde. It is of course within the ambit of the invention to at least slightly depart from the limits of this range. Using an amount of bromine below 0.45 mole per mole of benzaldehyde would result, however, in incomplete conversion of the starting material, and using an amount of bromine above 0.65 mole per mole of aldehyde would proportionately increase the formation of irrecoverable hydrobromic acid during bromination. The reaction is preferably carried out using 0.5 to 0.6 mole of bromine per mole of benzaldehyde.

The amount of oxidizing agent employed obviously depends upon the amount of bromine employed and upon the nature of the oxidizer. It is preferable that it should in any event be sufficient to ensure the additional bromination of the benzaldehyde formed by the hydrobromic acid which is produced. The amount of oxidizer would be expressed in the following in moles per mole of bromine, since the amount of hydrobromic acid which is formed naturally depends upon the amount of bromine employed.

When the oxidizing agent is hydrogen peroxide the amount of $H_2O_2$ is preferably close to the stoichiometric amount reflected by the reaction scheme (iii), namely, approximately 1 mole per mole of bromine. It is possible to vary somewhat from this amount without departing from the scope of the present invention.

In practice, this amount preferably ranges from 0.8 to 1.2 mole per mole of bromine and depends to some extent on the nature of the reaction medium and upon the acid employed. When an aqueous solution of hydrobromic acid is employed as the acid, a slight excess of hydrogen peroxide may be used. In the other cases, it is preferable not to exceed 1 mole of $H_2O_2$ per mole of bromine and even to operate using a slight deficiency of hydrogen peroxide.

The concentration of the aqueous solution of $H_2O_2$ employed is also not critical. Its selection is dictated by practical aspects which are well known to this art (for example, concern over not increasing the volume of the reaction mixture). In general, this concentration may range from 20 to 90% by weight of $H_2O_2$.

When an alkali metal hypochlorite is employed as the oxidizer, the bromination of the excess benzaldehyde by the HBr/hypochlorite pair or couple may be represented by the reaction scheme:

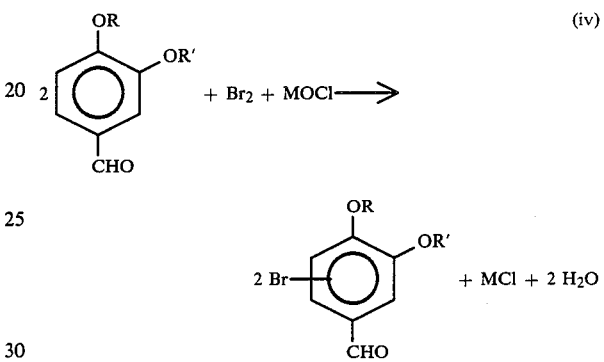

(iv)

in which M denotes an alkali metal. In this instance the amount of hypochlorite is also preferably close to that stoichiometrically required by the reaction, namely, 1 mole per mole of bromine. In practice, amounts of hypochlorite are used ranging from 0.7 to 1.1 mole per mole of bromine and preferably from 0.7 to 1 mole per mole of bromine. The concentration of the aqueous solutions of hypochlorite is also not critical.

When nitric acid is used as oxidizer, the reaction is represented by the following scheme:

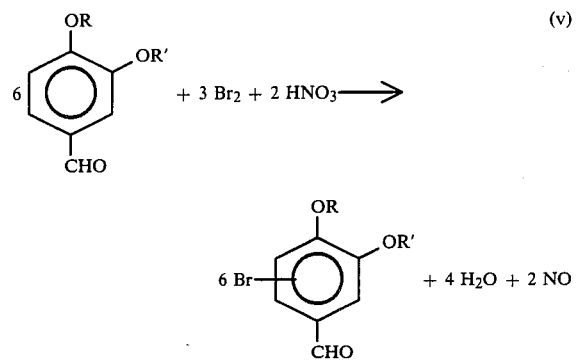

(v)

The amount of nitric acid employed to ensure the oxidation of the bromides to bromine is preferably approximately that amount stoichiometrically required by the reaction represented by the scheme (v), namely, close to $\frac{2}{3}$ of a mole of $HNO_3$ per 1 mole of $Br_2$. It is possible, however, to depart appreciably from the aforesaid stoichiometry without, nevertheless, departing from the scope of the invention. Thus, the amount of nitric acid may vary from 0.3 to 0.8 mole of $HNO_3$ per mole of bromine or, preferably, from 0.6 to 0.7 mole of $HNO_3$ per mole of bromine.

The concentration of the aqueous solution of nitric acid employed for completing the bromination too is not critical and may range from 20 to 90% by weight of $HNO_3$. Nevertheless, it is advantageous to employ concentrated solutions in order not to increase the volume of the reaction mixture. Solutions containing from 55 to 70% by weight of $HNO_3$ are especially suitable.

It has been found that it is advantageous to employ, jointly with the nitric acid, a small amount of nitrous acid which ensures a prompt starting of the reaction. In this instance, an alkali metal nitrite ($NaNO_2$, $KNO_2$) is used as an initiator. An amount on the order of 0.01 mole of nitrite per mole of aldehyde is sufficient to initiate the reaction. In general it is unnecessary to use more than 0.2 mole of nitrite per mole of benzaldehyde. Amounts ranging from 0.05 to 0.15 mole of nitrite per mole of benzaldehyde are especially suitable.

The temperature at which the bromination reaction is carried out advantageously ranges from 0° to 100° C. and preferably from 5° to 60° C.

Among the aldehydes of formula (I) which may be brominated by the process of the invention, exemplary are protocatechuic aldehyde (3,4-dihydroxybenzaldehyde), vanillin, ethylvanillin, isovanillin and veratraldehyde (3,4-dimethoxybenzaldehyde). Protocatechuic aldehyde, vanillin and ethylvanillin provide bromobenzaldehydes containing a bromine atom in a meta-position relative to the aldehyde group. Veratraldehyde is used to prepare 2-bromo-4-hydroxy-3-methoxybenzaldehyde and isovanillin to prepare 2-bromo-4-methoxy-5-hydroxybenzaldehyde. The process according to the invention is particularly highly suitable for the bromination of vanillin to 5-bromovanillin.

The present process is also particularly suitable for continuous operation.

In order to further illustrate the present invention and the advantages thereof, the following specific examples are given, it being understood that same are intended only as illustrative and in nowise limitative.

EXAMPLE 1

Anhydrous acetic acid (20 ml) followed by vanillin (7.5 g; 0.05 mole) were charged into a 100-ml round glass flask equipped with a stirring system, thermometer, a dropping funnel and cooled with a water bath at 20° C. Stirring was begun and then, when the vanillin had dissolved, a solution of bromine (4.8 g; 0.03 mole) in acetic acid (10 ml) was added dropwise. The temperature gradually increased to 30° C. When the bromine addition was complete, acetic acid (20 ml) was added, followed, dropwise, by hydrogen peroxide at a concentration of 30% of $H_2O_2$ (2.26 g; 0.02 mole). Stirring was continued for 10 min upon completion of the addition and the heterogeneous reaction mixture was cooled to 20° C. It was next filtered and the cake was washed on the filter with fresh acetic acid (10 ml) followed by ice water (30 ml). After drying under vacuum, a product (10.8 g) melting at 162° C. was obtained, in which 5-bromovanillin (10.60 g) was determined by high pressure liquid chromatography. Unconverted vanillin (0.45 g) was determined in the filtrate and the acetic acid wash.

The degree of conversion of vanillin was 94% and the yield of 5-bromovanillin relative to the vanillin converted was 98%.

EXAMPLES 2 AND 3

The procedure of Example 1 was repeated in 50 ml of acetic acid, but using the following vanillin/bromine/$H_2O_2$ molar ratios:

| EXAMPLES | Vanillin (moles) | $Br_2$ (mole) | $H_2O_2$ (mole) | DC (1) (%) | YC (2) (%) |
|---|---|---|---|---|---|
| 2 | 2 | 1 | 1.04 | 96.6 | 90 |
| 3 | 2 | 1.1 | 1 | 92.6 | 92.7 |

(1) Degree of conversion of vanillin;
(2) Yield of bromovanillin relative to vanillin converted.

EXAMPLE 4

A 2N aqueous solution of sulfuric acid (100 ml), followed by vanillin (15.15 g; 0.1 mole) were charged into a 250-ml round flask equipped as in Example 1. Stirring was begun and then bromine (9.6 g; 0.6 mole) was added dropwise to the vanillin suspension thus obtained; the temperature gradually increased to 30° C. When the addition was complete an aqueous solution containing 30.8% by weight of $H_2O_2$ (4.42 g, i.e. 0.04 mole) was introduced in the same manner. Upon completion of the addition, stirring was continued for an additional 5 min. The heterogeneous reaction mixture was cooled to 20° C. and then the solid phase was separated by filtration, washed on the filter with water and then dried at 60° C. under reduced pressure. The filtrate was extracted with methylene chloride (3×150 ml). The unconverted vanillin and the bromovanillin in the solid phase and in the methylene chloride washings was determined by high pressure liquid chromatography.

In this manner, 2.92 g of vanillin (i.e., a degree of conversion of 80.7%) and 16.42 g of 5-bromovanillin (0.071 mole), corresponding to a yield of 88.1% of theoretical relative to the vanillin converted, were determined.

EXAMPLE 5

Chloroform (110 ml) followed by vanillin (15.15 g) were charged into the apparatus of Example 4 and stirring was begun. When the vanillin had dissolved a 2N aqueous solution of $H_2SO_4$ (20 ml) was added. Bromine (9.6 g; 0.06 mole) was then added dropwise to the heterogeneous mixture thus obtained. The temperature gradually increased to 30° C. When the addition of bromine was complete, an aqueous solution containing 30% by weight of $H_2O_2$ (4.42 g, i.e., 0.04 mole) was charged in the same manner. The 5-bromovanillin which had precipitated as it was formed was separated off by filtration. The liquid phases of the filtrate were separated by decantation and the aqueous phase was extracted with methylene chloride (3×150 ml each time).

By employing the same procedure as in the previous examples, a total of 1.21 g of unconverted vanillin (corresponding to a degree of conversion of 92%) and 21.07 g of 5-bromovanillin, which represents a yield of 99.5% relative to the vanillin converted, were determined.

EXAMPLE 6

The procedure employed was under the same conditions as in Example 5, but with sulfuric acid replaced by a 2N aqueous solution of hydrobromic acid (50 ml), the volume of chloroform being 100 ml.

Under these conditions the degree of conversion of vanillin was 94.84% and the yield of 5-bromovanillin relative to the vanillin converted was 96.4%.

EXAMPLE 7

The procedure of Example 6 was repeated, except that a vanillin/bromine/$H_2O_2$ molar ratio of 2/1/1.1 was employed.

Under these conditions the degree of conversion of vanillin was 95.5% and the yield of 5-bromovanillin relative to the vanillin converted was 98.1%.

EXAMPLE 8

The procedure of Example 7 was repeated, except that the 2N hydrobromic acid was replaced by an aqueous solution containing 48% by weight of HBr (40 ml).

Under these conditions the degree of conversion of vanillin was 95.5% and the yield of 5-bromovanillin relative to the vanillin converted was 94.7%.

EXAMPLE 9

Example 7 was repeated, except that the temperature was permitted to increase to 50° C. at completion of the reaction.

Under these conditions the degree of conversion of vanillin was 94.8% and the yield of 5-bromovanillin relative to the vanillin converted was 95.7%.

EXAMPLE 10

Example 7 was repeated, except that the temperature was reduced to 0° C.

Under these conditions the degree of conversion of vanillin was 82.26% and the yield of 5-bromovanillin relative to the vanillin converted was 96.6%.

EXAMPLE 11

Example 7 was repeated, except that the hydrogen peroxide was replaced by $HNO_3$ (aqueous solution containing 65% by weight of $HNO_3$; 0.0187 mole) and sodium nitrite (0.01 mole).

Under these conditions the degree of conversion of vanillin was 75.6% and the yield of 5-bromovanillin relative to the vanillin converted was 91.02%.

EXAMPLE 12

Example 7 was repeated, except that the hydrogen peroxide was replaced by NaOCl (2N aqueous solution; 0.0277 mole).

Under these conditions the degree of conversion of vanillin was 76.8% and the yield of 5-bromovanillin relative to the vanillin converted was 89.2%.

EXAMPLE 13

The procedure of Example 7 was repeated, but with the bromine and hydrogen peroxide being added simultaneously.

Under these conditions the degree of conversion of vanillin was 97.4% and the yield of 5-bromovanillin relative to the vanillin converted was 94.1%.

EXAMPLE 14

Example 7 was repeated, except that the chloroform was replaced by isopropyl ether (250 ml).

Under these conditions the degree of conversion of vanillin was 86.2% and the yield of 5-bromovanillin relative to the vanillin converted was 94.1%.

EXAMPLE 15

The procedure of Example 7 was repeated, except that the 2N aqueous solution of HBr was replaced by a 0.5N aqueous solution of HBr (same volume: 50 ml).

Under these conditions a degree of conversion of vanillin of 71.5% and a yield of 5-bromovanillin relative to the vanillin converted of 86.2% were obtained.

EXAMPLE 16

The procedure of Example 7 was repeated, except that the 2N aqueous solution of HBr was replaced by water alone.

A degree of conversion of vanillin of 64.2% and a yield of 5-bromovanillin relative to the vanillin of 82.9% were obtained.

EXAMPLE 17

Example 11 was repeated, but with the addition of $HNO_3$ in the form of 65% strength aqueous solution (0.050 mole) and $NaNO_2$ (0.01 mole).

Under these conditions a degree of conversion of vanillin of 96.7% and a yield of 5-bromovanillin relative to the vanillin converted of 83% were obtained.

EXAMPLE 18

Example 13 was repeated, but with the addition of NaOCl (2N aqueous solution; 0.050 mole).

Under these conditions, the degree of conversion of vanillin was 81.1% and the yield of 5-bromovanillin relative to the vanillin converted was 85.7%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a substituted bromobenzaldehyde having the general formula:

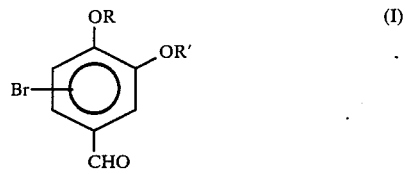

wherein R and R' are each hydrogen, methyl or ethyl, comprising (i) first brominating a substituted benzaldehyde having the general formula:

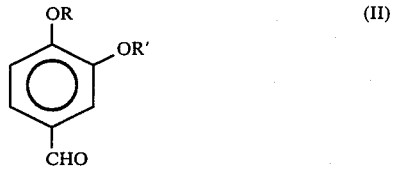

wherein R and R' are as defined above, with a less than stoichiometric amount of bromine, and (ii) completing said bromination reaction with a brominating agent couple which comprises (1) the hydrobromic acid generated in situ in the step (i) and (2) a bromide ion oxidizer.

2. The process as defined by claim 1, wherein said benzaldehyde (II) is simultaneously contacted with the less than stoichiometric amount of bromine and the oxidizer (2).

3. The process as defined by claim 1, wherein said bromination reaction is carried out successively by adding the oxidizer (2) to the step (i) reaction product.

4. The process as defined by claim 1, wherein said bromide ion oxidizer (2) comprises hydrogen peroxide, nitric acid or an alkali metal hypochlorite.

5. The process as defined by claim 1, wherein the less than stoichiometric amount of bromine ranges from 0.45 to 0.65 mole per mole of the benzaldehyde (II).

6. The process as defined by claim 1, wherein said brominating agent couple comprises hydrogen peroxide, the amount thereof ranging from 0.8 to 1.2 mole per mole of the bromine.

7. The process as defined by claim 1, wherein said brominating agent couple comprises nitric acid, the amount thereof ranging from 0.3 to 0.8 mole of $HNO_3$ per mole of the bromine.

8. The process as defined by claim 1, wherein said brominating agent couple comprises an alkali metal hypochlorite, the amount thereof ranging from 0.7 to 1.1 moles per mole of the bromine.

9. The process as defined by claim 1, said bromination being carried out in the presence of a carboxylic or inorganic acid.

10. The process as defined by claim 1, said bromination being carried out in a liquid alkanoic acid.

11. The process as defined by claim 10, said alkanoic acid comprising acetic acid.

12. The process as defined by claim 1, said bromination being carried out in an aqueous solution of sulfuric or hydrobromic acid.

13. The process as defined by claim 1, said bromination being carried out in an inert, water-immiscible organic solvent for the benzaldehyde (II) and for the bromine, and in the presence of an aqueous solution of sulfuric or hydrobromic acid.

14. The process as defined by claim 1, wherein the bromine substituent of the bromobenzaldehyde (I) is in the meta-position relative to the aldehyde function.

15. The process as defined by claim 1, wherein the benzaldehyde of the general formula (II), R is hydrogen and R' is hydrogen, methyl or ethyl.

16. The process as defined by claim 1, wherein said benzaldehyde (II) comprises protocatechuic aldehyde, vanillin, isovanillin, ethylvanillin or veratraldehyde.

17. The process as defined by claim 1, wherein said bromobenzaldehyde (I) comprises 5-bromovanillin.

* * * * *